(12) United States Patent
Fieselmann

(10) Patent No.: US 10,977,790 B2
(45) Date of Patent: Apr. 13, 2021

(54) METHOD AND DEVICE FOR DETERMINING RESULT VALUES ON THE BASIS OF A SKELETAL MEDICAL IMAGING RECORDING

(71) Applicant: Siemens Healthcare GmbH, Erlangen (DE)

(72) Inventor: Andreas Fieselmann, Erlangen (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 72 days.

(21) Appl. No.: 16/392,981

(22) Filed: Apr. 24, 2019

(65) Prior Publication Data

US 2019/0347791 A1 Nov. 14, 2019

(30) Foreign Application Priority Data

May 8, 2018 (EP) .................................. 18171283

(51) Int. Cl.
| | | |
|---|---|---|
| *G06T 7/00* | (2017.01) | |
| *G16H 15/00* | (2018.01) | |
| *G06K 9/00* | (2006.01) | |

(52) U.S. Cl.
CPC ........ *G06T 7/0012* (2013.01); *G06K 9/00536* (2013.01); *G16H 15/00* (2018.01);
(Continued)

(58) Field of Classification Search
CPC ......... G06T 7/0012; G06T 2207/10116; G06T 2207/30008; G06T 2207/10081; G06T 2207/10088; G06T 2207/10132; G06T 7/60; G16H 15/00; G16H 30/40; G16H 50/30; G16H 30/20; G06K 9/00536;
(Continued)

(56) References Cited

U.S. PATENT DOCUMENTS 7,157,696 B2 * 1/2007 White .................... A61B 6/583
250/252.1
2007/0197902 A1 8/2007 Friedlander et al.
(Continued)

FOREIGN PATENT DOCUMENTS

DE    102007007803 A1   8/2008
WO    WO 2006000063 A1   1/2006

OTHER PUBLICATIONS

Tao, et al, "Robust Learning-Based Parsing and Annotation of Medical Radiographs", IEEE Transactions on Medical Imaging, vol. 30, No. 2, Feb. 2011, pp. 338-350; 2011.
(Continued)

*Primary Examiner* — Neil R McLean
(74) *Attorney, Agent, or Firm* — Harness, Dickey & Pierce, P.L.C.

(57) ABSTRACT

A method is for determining result values based upon a skeletal medical imaging recording. In an embodiment, the method includes providing a skeletal medical imaging recording; automatically determining reference points in the image recording; and calculating an orthopedic result value based at least upon a spacing between two reference points and/or upon an angle defined by reference points. A corresponding device, a corresponding diagnostic station for the assessment of a skeletal medical imaging recording and a corresponding medical imaging system also are disclosed in embodiments.

25 Claims, 7 Drawing Sheets

(52) U.S. Cl.
CPC ........... *G06T 2207/10116* (2013.01); *G06T 2207/30008* (2013.01)

(58) Field of Classification Search
CPC ..... A61B 6/032; A61B 5/1071; A61B 5/1072; A61B 5/4585; A61B 5/7264; A61B 6/505; A61B 5/055; A61B 6/5211
See application file for complete search history.

(56) References Cited

U.S. PATENT DOCUMENTS

| | | | |
|---|---|---|---|
| 2008/0212741 | A1 | 9/2008 | Haras |
| 2017/0196526 | A1* | 7/2017 | Fieselmann ......... G06K 9/00362 |
| 2018/0061090 | A1 | 3/2018 | Jerebko et al. |

OTHER PUBLICATIONS

Philips, C. L. et al.:"The measurement of patellar height"; In: The Bone and Joint Journal of Surgery (Br); vol. 92-B; No. 8; pp. 1045-1053; 2010; DOI: https://doi.org/10.1302/0301-620X.92B8.23794.

Goossen, A. et al.: "Automatic Joint Alignment Measurements in Pre- and Post-operative Long Leg Standing Radiographs"; in: Methods of Information in Medicine; vol. 51; No. 5; pp. 406-414; 2012; DOI: https://doi.org/10.3414/ME11-02-0033.

Chi-Wen Hsieh et al: "Bone age estimation based on phalanx information with fuzzy constrain of carpals"; Medical & Biological Engineering & Computing, Springer, Berlin, DE, Bd. 45, Nr. 3, Jan. 23, 2007 (Jan. 23, 2007), pp. 283-295, XP019864828, ISSN: 1741-0444, DOI: 10.1007/S11517-006-0155-9;2007.

Gąciarz, Tomasz et al:"Automated Assessment of Hallux Valgus in Radiographic Images"; in: Tavares J., Natal Jorge R. (eds) VipIM-AGE 2017. ECCOMAS 2017. Lecture Notes in Computational Vision and Biomechanics; vol. 27; 2018; DOI: https://doi.org/10.1007/978-3-319-68195-5_68.

European Search Report with Application No. 18171283.7 dated Nov. 15, 2016.

European office Action dated Dec. 3, 2019.

* cited by examiner

METHOD AND DEVICE FOR DETERMINING RESULT VALUES ON THE BASIS OF A SKELETAL MEDICAL IMAGING RECORDING

PRIORITY STATEMENT

The present application hereby claims priority under 35 U.S.C. § 119 to European patent application number EP 18171283.7 filed May 8, 2018, the entire contents of which are hereby incorporated herein by reference.

FIELD

Embodiments of the invention generally relate to a method and a device for determining result values on the basis of a skeletal medical imaging recording. Embodiments of the invention further generally relate to a corresponding diagnostic station for the assessment of a skeletal medical imaging recording and a corresponding medical imaging system.

BACKGROUND

In (musculo)skeletal radiology, length and angle measurements are often carried out on bones. For example, in the knee joint, various spacings and angles are measured on the patella, femur and tibia in order to diagnose misalignments there, to determine suitable treatment measures or to monitor a therapeutic process. Typically, the following procedure is followed for these measurements:

Firstly, the measurement of the relevant images is carried out by a diagnostician, e.g. a physician. In this context, particular lengths and angles are measured in the images and from these measurements, parameters are calculated, for example a ratio of two lengths. A parameter of this type is designated below an "orthopedic result value". The lengths and angles are taken from reference points in the images, which are also designated (anatomical) "landmarks". The measurement is, in practice, performed manually and, with digital images, is typically supported by the measuring tool (e.g. a spacing measuring function) of an image review software.

Following the measurement, a classification of the measurement results making use of previously stipulated normal ranges takes place. These normal ranges are compared with the orthopedic result value determined during the measurement and thereafter, it is decided into which classification the measured image section is to be placed.

Following the classification, the creation of a report or a documentation of the measurement results and the classifications take place.

A severe disadvantage of the known procedure is that physicians, such as for example radiologists, orthopedics specialists or surgeons must carry out the measurements manually. For the physician, a manual procedure of this type is time-consuming and is also often disliked. In addition, a manual procedure demands a not inconsiderable amount of time, which has negative consequences on the costs of an examination, not least for a patient.

A further disadvantage of a manual measurement and evaluation is that the aforementioned normal ranges depend on different factors, for example the normal ranges are age-dependent. Thus, for a manual procedure, an external reference must often be called upon by the diagnosing physician to look up the normal ranges, which can lead to errors which result, for example, from an incorrect reading or recording of values.

In addition, during monitoring of the progress of a treatment in which a plurality of recordings is usually made over a particular time period, it has a negative effect if different recordings are carried out and evaluated by different physicians. Because of the manual evaluation, the measuring results can be subjectively influenced, which can lead to the interpretation of the measuring results, for example the recognition of a change over a particular time period, becoming more difficult.

SUMMARY

At least one embodiment of the present invention provides an alternative, convenient method and a corresponding device for determining result values on the basis of a skeletal medical imaging recording and a corresponding diagnostic station for the assessment of a skeletal medical imaging recording and a corresponding medical imaging system, with which the aforementioned disadvantages can be avoided.

Embodiments of the present invention are directed to a method, a device, a diagnostic station and a medical imaging system.

At least one embodiment of the invention is directed to a method for determining result values on the basis of a skeletal medical imaging recording, comprising:
 providing the skeletal medical imaging recording;
 automatically determining reference points in the skeletal medical imaging recording; and
 calculating an orthopedic result value based upon at least one of a spacing between two reference points of the reference points determined, and an angle defined by the reference points determined.

At least one embodiment of the invention is directed to a device for determining result values based upon a skeletal medical imaging recording, comprising
 a data interface configured to acquire image data of the skeletal medical imaging recording;
 a reference point determining unit configured to automatically determine reference points in the skeletal medical imaging recording; and
 a result value ascertaining unit configured to calculate an orthopedic result value based upon at least one of a spacing between two reference points of the reference points determined, and an angle defined by the reference points determined.

An inventive diagnostic station of at least one embodiment for assessment of a skeletal medical imaging recording is equipped for carrying out at least one embodiment of an inventive method. Alternatively or additionally, it comprises a device according to at least one embodiment of the invention.

The diagnostic station of at least one embodiment, can be connected via data technology in the context of an RIS with a medical imaging recording unit or a PACS or it is at least equipped for an integration into an RIS or for a connection via data technology to a medical imaging recording unit or a PACS.

An inventive medical imaging system of at least one embodiment comprises at least one embodiment of an inventive device, in particular at least one embodiment of an inventive diagnostic station.

In this respect, at least one embodiment is also directed to a corresponding computer program product with a computer program which is loadable directly into a computer system or a storage apparatus of a diagnostic station, having program portions in order to carry out all the steps of at least one embodiment of the method according to the invention when the program is executed in the computer system or the diagnostic station. Such a computer program product can comprise, where relevant, in addition to the computer program, additional components, such as for example, documentation and/or additional components including hardware components, for example hardware keys (dongles, etc.) in order to use the software.

For transport to the computer system and/or to the diagnostic station and/or for storage at or in the computer system and/or the diagnostic station, a computer-readable medium, for example a memory stick, a hard disk or another transportable or firmly installed data carrier, can be used on which the program portions of the computer program which are readable and executable by a computer system or a computer unit of the diagnostic station are stored. For this, the computer unit can have, for example, one or more cooperating microprocessors or the like.

BRIEF DESCRIPTION OF THE DRAWINGS

The invention will now be described again in greater detail using example embodiments by reference to the accompanying drawings. In the various drawings, the same components are provided with identical reference characters. The drawings are in general not to scale. In the drawings.

DETAILED DESCRIPTION OF THE EXAMPLE EMBODIMENTS

Figure 1:
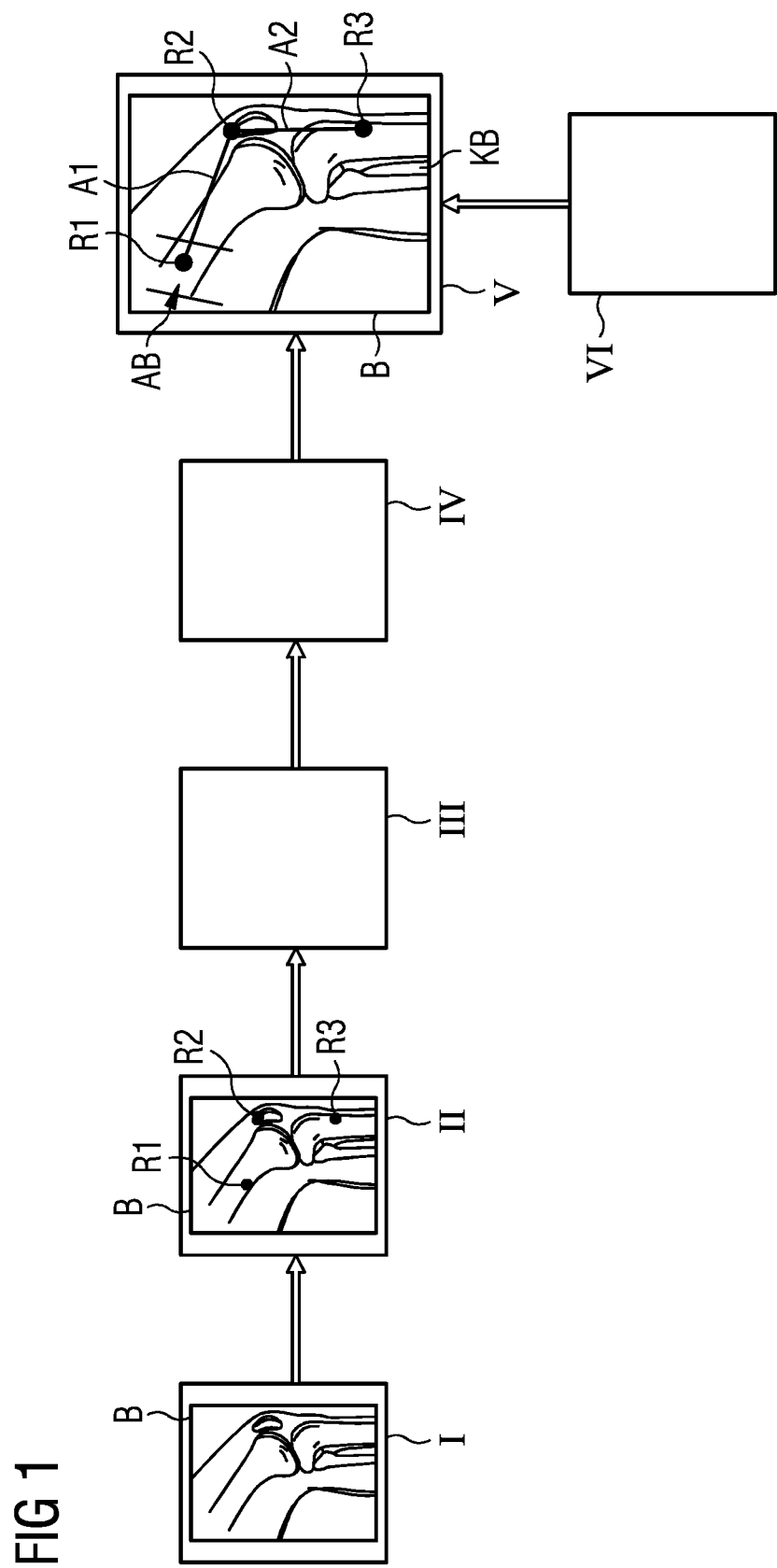
FIG. 1 is a block diagram of a preferred embodiment of the inventive method.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the inventive method and/or the inventive device serve to determine result values on the basis of a skeletal medical imaging recording, in particular an automated measurement and possibly also a classification and/or a possible visualization of the influence of the positioning of the measuring points on the result values. Such image recordings can be both projection images, for example recorded by way of a radiography system, as well as tomographic image data, for example recorded via CT, MRT, cone-beam CT or ultrasound. It is essentially irrelevant how the image recordings have been made provided the regions of relevance for an examination are discernible. The result values are determined on the basis of data which results from the image recordings, in particular directly from the image data (e.g. for digital image recordings) or from data resulting from a coordinate system that is projected over the image recording (e.g. for analog image recordings).

At least one embodiment of the invention is directed to a method for determining result values on the basis of a skeletal medical imaging recording, comprising:

providing a skeletal medical imaging recording, automatically determining reference points in the image recording, and calculating an orthopedic result value based at least upon a spacing between two reference points and/or upon an angle defined by reference points.

In at least one embodiment, the method comprises:

Providing an Image Recording

In this step, a skeletal medical imaging recording is provided. This can be carried out in that an image recording is provided for the method, that is, recorded by an imaging system and, if relevant, the image recording is reconstructed from raw data. However, the image recording can also be older and made available, for example, via a radiology information system ("RIS") from a PACS (Picture Archiving and Communication System). The image recordings can be two-dimensional or three-dimensional. The provision and the steps described below can also take place in the context of Cloud Computing, as described in greater detail below.

Determining Reference Points

In this step, an automatic determination of reference points in the image recording takes place. An automatic determination can preferably be achieved by way of an algorithm which is based on the principles of machine learning. This takes place particularly preferably via an inventive device as described below. With the determination of the reference points, their coordinates in the image recording (e.g. pixel positions in the image or in a coordinate system projected onto the image) are known to the method.

Calculating a Result Value

In this step, an orthopedic result value is calculated. The expression "orthopedic result value" implies that it represents orthopedically relevant values which are the result of the calculation carried out. The calculation is based at least upon a spacing between two reference points and/or upon an angle defined by reference points. The angle can be defined, for example, as an angle in a triangle which is generated by the three reference points, with one of the reference points as the apex of the angle. However, the angle can, for example, also be defined with four reference points, where two pairs of points each define a straight line, the lines intersecting one another at an angle.

Spacings and/or angles are calculated using the known coordinates of the reference points (see previous step). Subsequently, for example, from the spacings, a spacing ratio can be determined as a result value.

The device according to at least one embodiment of the invention comprises:

A Data Interface for Acquiring Image Data of a Skeletal Medical Imaging Recording This can be either a normal data interface in the context of an RIS or PACS, or a data interface (e.g. a data bus) in a medical imaging system which, for example, directly acquires image data from an image reconstruction unit or an image detector. This data interface can however also acquire image data from a scanner by which analog image recordings can be scanned in. By way of a digital transfer of an image recording, a coordinate system is automatically available, specifically the position of the pixels in the image recording. This coordinate system can be transformed, if relevant, by way of a transformation unit, e.g. to the true size of the recorded region or into spatial coordinates of the patient.

A Reference Point Determining Unit Configured for an Automatic Determination of Reference Points in the Image Recording.

For this purpose, the reference point determining unit preferably comprises an algorithm trained in the context of machine learning, preferably a neural network. The automatic determination of reference points in the image recording can be carried out by this algorithm.

A Result Value Ascertaining Unit Configured for a Calculation of an Orthopedic Result Value Based at Least Upon a Spacing Between Two Reference Points and/or Upon an Angle Defined by Reference Points (See Above).

An inventive diagnostic station of at least one embodiment for assessment of a skeletal medical imaging recording is equipped for carrying out at least one embodiment of an inventive method. Alternatively or additionally, it comprises a device according to at least one embodiment of the invention.

The diagnostic station of at least one embodiment, can be connected via data technology in the context of an RIS with a medical imaging recording unit or a PACS or it is at least equipped for an integration into an RIS or for a connection via data technology to a medical imaging recording unit or a PACS.

An inventive medical imaging system of at least one embodiment comprises at least one embodiment of an inventive device, in particular at least one embodiment of an inventive diagnostic station.

A majority of the aforementioned components of the device or the diagnostic station can be realized entirely or partially in the form of software modules in a processor of a corresponding device or diagnostic station. A realization largely through software has the advantage that conventionally used devices and diagnostic stations can easily be upgraded with a software update in order to operate in the manner according to at least one embodiment of the invention.

In this respect, at least one embodiment is also directed to a corresponding computer program product with a computer program which is loadable directly into a computer system or a storage apparatus of a diagnostic station, having program portions in order to carry out all the steps of at least one embodiment of the method according to the invention when the program is executed in the computer system or the diagnostic station. Such a computer program product can comprise, where relevant, in addition to the computer program, additional components, such as for example, documentation and/or additional components including hardware components, for example hardware keys (dongles, etc.) in order to use the software.

For transport to the computer system and/or to the diagnostic station and/or for storage at or in the computer system and/or the diagnostic station, a computer-readable medium, for example a memory stick, a hard disk or another transportable or firmly installed data carrier, can be used on which the program portions of the computer program which are readable and executable by a computer system or a computer unit of the diagnostic station are stored. For this, the computer unit can have, for example, one or more cooperating microprocessors or the like.

Further particularly advantageous embodiments and developments of the invention are disclosed by the claims and the following description, wherein the claims of one claim category can also be further developed similarly to the claims and description passages relating to another claim category and, in particular, also individual features of different example embodiments or variants can be combined to new example embodiments or variants.

As already noted above, the method can also comprise elements of "cloud computing". In "cloud computing", an IT infrastructure, e.g. storage space or computing power, but also application software, is made available via a network. The communication between the user and the cloud takes place via data interfaces and data transfer protocols.

Within the context of cloud computing, in a preferred embodiment of the inventive method, a provision of a skeletal medical imaging recording takes place via a data channel (e.g. a network) to a cloud. This cloud comprises a (remote) computer system, e.g. a computer cluster which typically does not comprise the computer of the user. This cloud can be made available, in particular, by the medical institution which also provides the medical imaging systems. In particular, the data of the image recording is transmitted via an RIS or PACS to a (remote) computer system (the cloud). Preferably, the computer system of the cloud, the network and the medical imaging system represent a group in the data technology sense. The method can be realized by way of a command combination in the network.

The automatic determination of reference points is preferably carried out in the cloud. Preferably, however, the user can have already undertaken a processing of the image recording on his local computer (including in the context of the inventive method), e.g. in that he has entered or allowed to be calculated (perhaps roughly) some reference points in a preliminary representation.

A calculation of an orthopedic result value also preferably takes place in the cloud although, depending on the case and complexity of the calculation, it can also be performed on the local computer of the user (e.g. in the context of the aforementioned preliminary processing or on the basis of spacings/angles communicated by the cloud). In the cloud, preferably at least required spacings and/or angles are determined.

The data or results of the data calculated in the cloud are preferably transmitted again via a data channel (e.g. a network) to the local computer of the user. In the example discussed above, the data of the image recording provided is therefore processed by a computer system of a hospital according to the inventive method and the results of this processing (that is, the spacings and/or angles together with the coordinates of the reference points and/or the result values) are returned again via an RIS or PACS to the user.

In the context of a preferred embodiment of the device according to the invention, the aforementioned units (data interface, reference point determining unit and, in particular, also the result value ascertaining unit) are present at the cloud. A preferred ascertaining system comprises, in addition to such a device, a local computer unit which is connected via a data channel (e.g. a network, in particular configured as an RIS or a PACS) to the device, wherein the local computer unit comprises at least one data gathering interface in order to receive data (in particular regarding spacings and/or angles together with the coordinates of reference points and/or the result values). It is also preferred if the local computer also comprises a transmitting interface in order to transmit data to the device. However, this transmitting interface is not absolutely necessary if an architecture of the data channel exists which enables a recording of a medical imaging system (e.g. an X-ray device) together with an information item regarding the type of the desired result values to be made available to the device directly.

It can be advantageous in the context of the aforementioned embodiments that the computing power made available depends on the identity or selection of the user. For example, the algorithms usable for determining the reference points and/or spacings/angles can have different complexities and can deliver differingly precise results. The user can preferably select the degree of processing by the cloud, in particular which algorithm is to be used or which quality level the result is to have. For example, for a coarse overview, the quality demanded is relatively low, so that a "fast" algorithm can be selected to obtain a result as quickly as possible.

As was addressed above, for the automatic determination of the reference points, an algorithm trained within the context of machine learning can be used, preferably a neural network, in particular configured for Deep (machine) Learning. The automatic determination of reference points in the image recording is then performed by this algorithm. The algorithm is thereby trained before the determination of result values on the basis of a plurality of skeletal medical imaging recordings.

For the training, a large number of image recordings with already entered reference points, e.g. X-ray images with reference points specified by radiologists, is advantageously used. The reference points should have been entered as accurately as possible, so that the training can take place in a temporally optimized manner. An algorithm trained in this way can then generate reference points on new skeletal image recordings automatically.

Preferable in this context is a training method for establishing a reference point determining unit for a device according to an embodiment of the invention, comprising the steps:

providing a learning computer device, wherein the learning computer device is configured to train an algorithm that is trainable in the context of machine learning, preferably a neural network, on the basis of image recordings with reference points entered, providing a reference point determining unit comprising such an algorithm which however is untrained or at least is not optimally trained, on or at the learning computer device.

providing a plurality of image recordings with reference points entered, training the algorithm of the reference point determining unit according to the principle of machine learning, in particular on the basis of the recognition of the reference points in the image recordings and the allocation of patterns in the image recordings to the positions of the reference points.

Preferable in this regard is also a learning computer device comprising a processor and a data store with instructions which enable the processor on their execution:

to acquire skeletal medical imaging recordings, with reference points entered, that have been provided to the computer device.

to recognize the reference points in the image recordings as objects.

to train an aforementioned algorithm according to the principle of machine learning, preferably on the basis of the recognition of the reference points in the image recordings and the allocation of patterns in the image recordings to the positions of the reference points.

A preferred method additionally comprises the following steps:

displaying the image recording together with reference points and preferably also of spacings and/or angles. This representation takes place in the context of a monitoring image. The monitoring image thus comprises the image recording and the additionally represented components in the form of image information.

providing a manual displacement capability for the reference points in the monitoring image. The displacement capability should be understood here to be a function (or a unit) which enables a user to displace reference points in the monitoring image. For this, the displacement capability preferably comprises a request for a displacement command and/or a confirmation command which brings about a displacement or placement of a reference point.

A preferred device comprises, for this, an output data interface for the output of image data of a monitoring image to an image display unit.

A particularly preferred device further comprises a displacement unit that is configured for a manual displacement capability for the reference points in the monitoring image. This should be understood, in particular, as a unit which is configured to process a query of a displacement command and a confirmation command and, dependent upon these commands, to position a reference point in the monitoring image.

Preferably, for one, in particular for each, reference point, a reference value dependency RWA is determined. This reference value dependency RWA represents the dependency of an orthopedic result value on a spatial displacement of the reference point. For example, the reference value dependency RWA states by how much the result value would deviate if a reference point were displaced by a (small) displacement vector $\hat{s}$. It can thereby be estimated how accurately the result value has been calculated, even if the reference points had not been optimally positioned.

The determined reference value dependency RWA is preferably visualized with the reference point (or the relevant reference points), in particular as a component in the aforementioned monitoring image. The reference value dependency can be therein represented as actual values which can also be designated "reference value dependency values", as a group of points which are arranged round a reference point in a cloud of points according to the displacement vector in question, and represent the respective reference value dependency at this point. The reference value dependency can however also be visualized in the form of other graphical elements, for example lines, color markings or shading. Particularly preferably, the method also offers the aforementioned displacement capability.

A preferred device comprises for this purpose a reference value dependency determining unit for determining a reference value dependency RWA for a reference point.

With regard to the determination of the reference value dependency RWA for a reference point, preferably, the following steps are performed:

a basic result value is formed from a group of reference points relevant for the orthopedic result value in question.

a comparison result value is formed from the group of reference points of relevance for the orthopedic result value in question, wherein the reference point for which the reference point dependency RWA is determined is displaced for the calculation of the comparison result value (by the aforementioned displacement vector $\hat{s}$).

This can be carried out for all the relevant reference points.

Preferably, an absolute reference value dependency aRWA can be determined. This is preferably determined from the difference of the comparison result value and the basic result value.

Particularly preferably, a relative reference value dependency rRWA is determined from the absolute reference value dependency aRWA. This takes place in particular in that the absolute reference value dependency aRWA is normalized by way of a basic result value.

The basic result value and the comparison result value are preferably calculated in the same way as the orthopedic result value.

The reference value dependency RWA is calculated, for example, based upon a result value $M=M(L_1, L_2, \ldots, L_N)$ for a number of N reference points with the coordinates ($L_1, L_2, \ldots, L_N$). As far as the result value M is concerned, there exists a plurality of different measurements which can be carried out on X-ray pictures. The type of the measurement depends, for example, on the diagnostic request or the body region. The function is a mathematical description of the scan. For a current orthopedic scan for determining the Insall-Salvati index, the following would, for example, apply: $M(L_1, L_2, L_3) = |L_1 - L_2|/|L_2 - L_3|$.

An absolute reference value dependency aRWA for the k-th reference point Rk with the displacement vector $\hat{s}$ is given, for example, according to $$aRWA(k,\hat{s}) = M(\acute{L}_1, \acute{L}_2, \ldots, \acute{L}_N) - M(L_1, L_2, \ldots, L_N) \quad (1)$$

where $\acute{L}_i = L_i$ if $i \neq k$ and $\acute{L}_i = L_i + \hat{s}$ if $i = k$.

The relative reference value dependency rRWA for the k-th reference point Rk is then calculated from the absolute reference value dependency aRWA, for example, according to $$rRWA(k,\hat{s}) = aRWA(k,\hat{s})/M(L_1, L_2, \ldots, L_N). \quad (2)$$

Preferably, for a (relative) reference value dependency RWA for a reference point, isolines are determined (and possibly also visualized). These isolines identify the positions of reference points which correspond to a particular, possibly absolute, but preferably percentage, change of the orthopedic result value. Regarding the preceding example for calculating the (relative) reference value dependency RWA, then for determining the isolines, different reference value dependencies are calculated with different displacement vectors. However, the formulae can also be transposed and, for a fixed (possibly percentage) change, the quantity of the displacement vectors determined which would lead to such a (possibly percentage) change. With regard to the isolines, reference is made to the examples below.

These isolines are preferably visualized or displayed in a monitoring image (e.g. as values which can also be designated "reference value dependency values" or in the form of graphical elements) and serve in this way as an indication of what influence displacements of reference points could have.

Preferably, for a (relative) reference value dependency RWA for a reference point, a local acceptance range is determined (and possibly also visualized). This local acceptance range identifies that range within which a displacement of the reference point brings about a relative change of the orthopedic result value within a predetermined global acceptance range. With regard to the local acceptance range, reference is made to the examples below.

This local acceptance range is preferably visualized or displayed in a monitoring image (e.g. as values which can also be designated "reference value dependency values" or in the form of graphical elements), in particular with a (color) identification and serves in this way as an indication of what displacements of reference points would be acceptable.

Preferably, an automatic classification at least of parts of the skeletal medical imaging recording is additionally carried out on the basis of the orthopedic result values by way of normal ranges. This classification classifies the image part in question according to medical criteria, by which for example, a misalignment, an enlargement or a diminution of a body region can be detected.

The classification preferably takes place on the basis of limit values which define the normal ranges. The limit values are particularly preferably provided in a database. If, for example, the case arises that a result value has been ascertained which lies below a limit value G, then the result value would be unremarkable. If, however, the result value is equal to or exceeds G, then a particular pathology could be present which could also be clearly defined medically with the selected limit value. The normal ranges or limit values can be patient-dependent. For example, normal ranges or limit values can be age-dependent, weight-dependent, height-dependent or sex-dependent.

Preferably, for a (relative) reference value dependency RWA for a reference point, class limits are determined (and possibly also visualized). These class limits identify the regions within which displacements of the reference point in question merely bring about (in particular relative) changes in the orthopedic result value which lie within a classification. With regard to the class limits, reference also is made to the examples below.

These class limits are preferably visualized or displayed in a monitoring image (e.g. as values which can also be designated "reference value dependency values" or in the form of graphical elements) and serve in this way as an indication of what influence displacements of reference points could have. For example, with a non-optimally positioned reference point, it could be recognizable at a glance whether a readjustment of the position should take place or whether the effort for this would be unnecessary, since no change to the classification would arise therefrom.

A preferred device in this context comprises a visualization unit for visualizing isolines and/or a local acceptance range and/or class limits. This visualization unit can be configured as a control device for controlling a display unit, e.g. a monitor. This control device is configured for controlling the display unit such that isolines and/or a local acceptance range and/or class limits are displayed.

A combination of the above-described displacement capability with a display of the isolines and/or the local acceptance range and/or the class limits is preferred, whereby particularly preferably with each displacement step, the isolines and/or the local acceptance range and/or the class limits are calculated anew, since they can change due to the displacement of a reference point, including for other reference points.

According to a preferred method of an embodiment, an automatic generation of a report takes place. This report contains information items belonging to the group
orthopedic result values,
spacings,
angles,
coordinates of the reference points,
a classification, and preferably
further patient-specific information items.

Herein, preferably a computer-readable file is generated, for example a pdf file which contains the information in table form and/or the reference points or spacings and/or angles as figures. A preferred device comprises, in this regard, a report creation unit and, in particular, a software library, wherein the report creation unit is configured to generate a file with the report in question.

FIG. 1 shows a block diagram of a preferred embodiment of the inventive method for determining result values on the basis of a skeletal medical imaging recording B.

In step I, a provision of a skeletal medical imaging recording B takes place, whereby here the recording of a human knee is shown.

In step II, an automatic determination of reference points R1, R2, R3 in the image recording B, shown here as circles, takes place.

In step III, a calculation of an orthopedic result value OE based at least upon a spacing A1, A2 between two reference points R1, R2, R3 and/or upon an angle defined by reference points R1, R2, R3 takes place.

In step IV, a determination of one reference value dependency RWA for each of the reference points R1, R2, R3 determined in step II takes place.

This reference value dependency RWA is determined for one of the reference points R1, R2, R3 so that based upon the calculation of the orthopedic result value OE, a basic result value is calculated and a comparison result value is calculated, whereby for the calculation of the comparison result value, the observed reference point R1, R2, R3 is displaced by a displacement vector. From the difference between the basic result value and the comparison result value normalized to the basic result value, there then results the reference value dependency RWA, which in this case is a relative reference value dependency rRWA.

In step V, a display of a monitoring image KB which comprises the image recording B together with reference points R1, R2, R3 and spacings A1, A2 takes place and additionally comprises an acceptance range AB derived from the reference value dependency RWA.

In step VI, a manual displacement capability for the reference points R1, R2, R3 in the monitoring image KB is made available which permits the user to displace the reference points R1, R2, R3 as desired. Preferably, on a displacement, a renewed determination and visualization of the relative reference value dependency rRWA takes place in the monitoring image on the basis of the displaced reference points R1, R2, R3.

Figure 2:
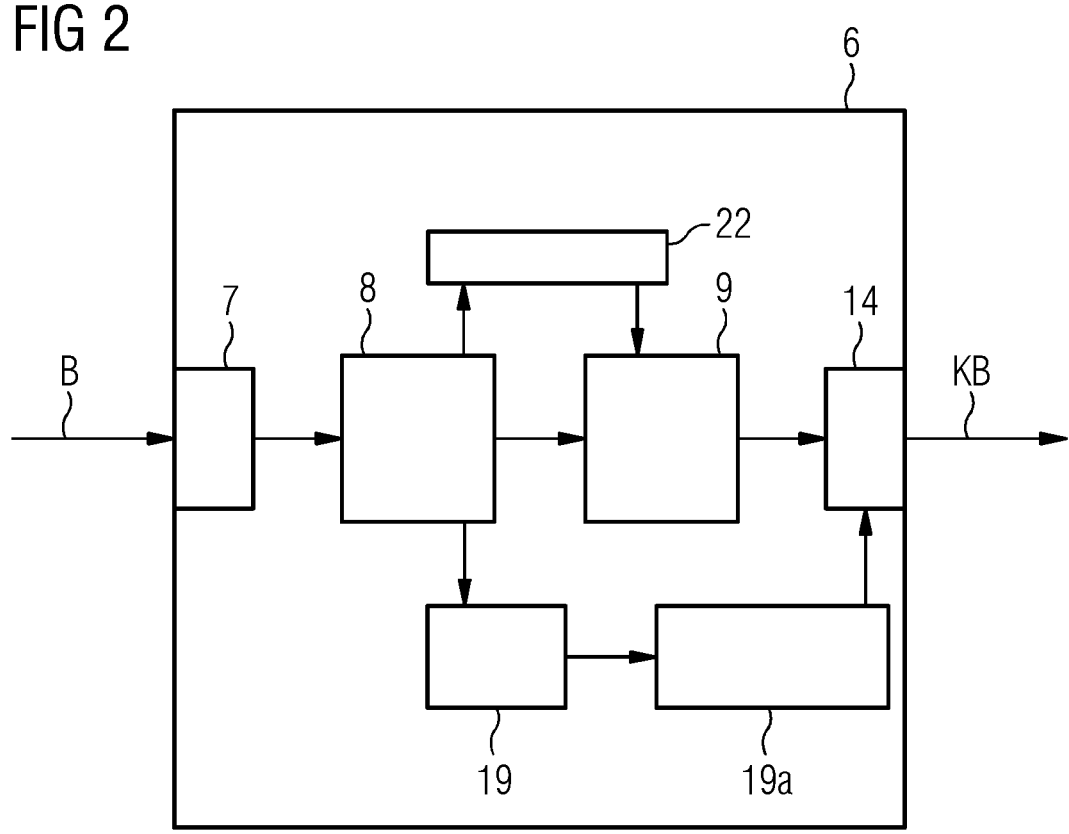
FIG. 2 is a representation of a preferred device.

FIG. 2 shows in an outline form a preferred device 6 for determining result values OE on the basis of a skeletal medical imaging recording B. This device 6 comprises the following components:

A data interface 7 for acquiring image data of a skeletal medical imaging recording B, for example via a radiology information system (RIS) from a PACS (picture archiving and communication system) or a medical imaging recording apparatus. Since the data in this example is of a digital nature, the image recording B can be made equivalent here to the image data.

A reference point determining unit 8 configured for an automatic determination of reference points R1, R2, R3 in the image recording B.

A result value ascertaining unit 9 configured for a calculation of an orthopedic result value OE based at least upon a spacing A1, A2 between two reference points R1, R2, R3 and/or upon an angle defined by reference points R1, R2, R3.

Figure 7:
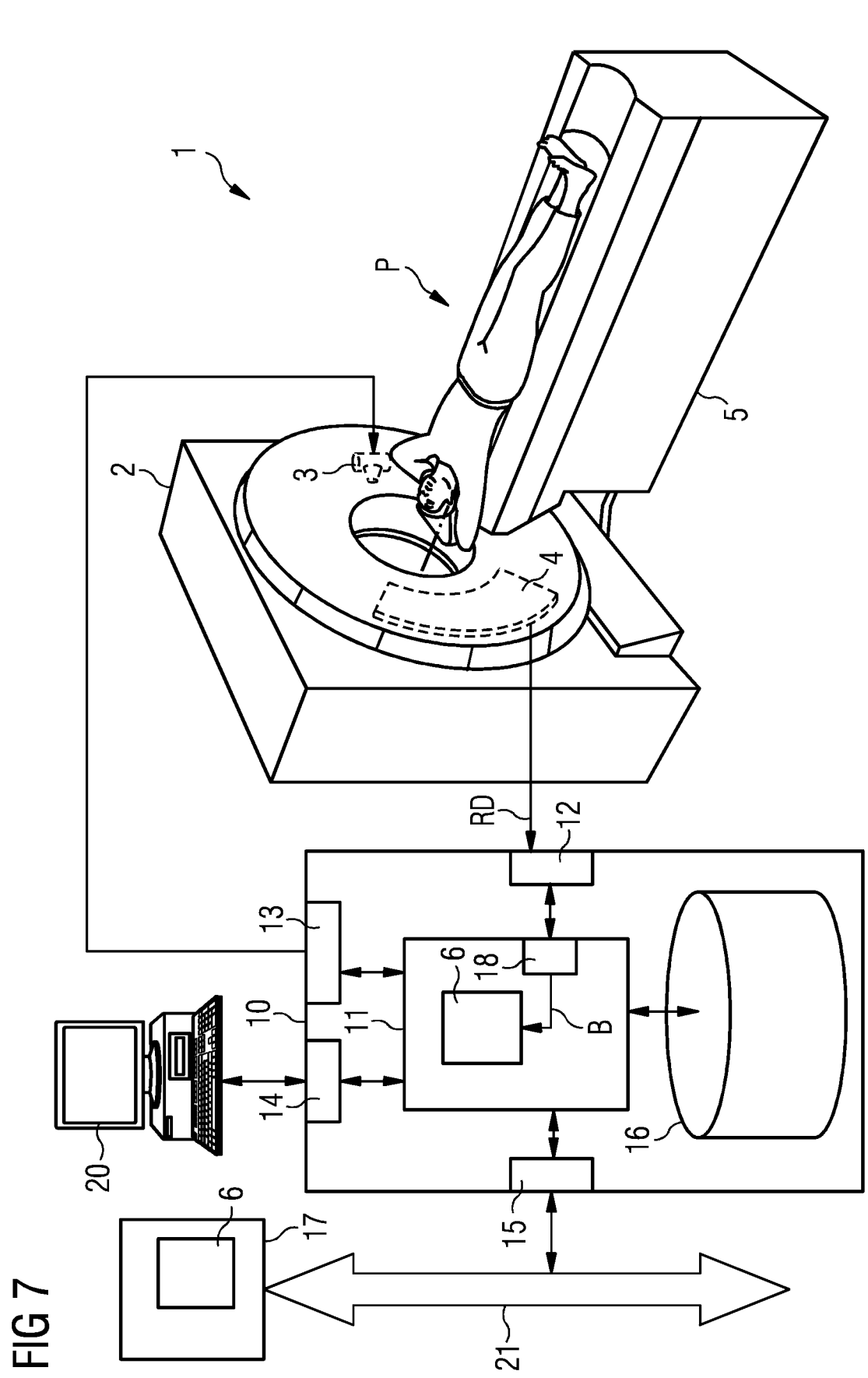
FIG. 7 is a rough schematic representation of an imaging system with an example embodiment of an inventive control device for carrying out the method.

The device 6 additionally comprises the following components which are essentially optional:

An output data interface 14 for the output of image data of a monitoring image KB to an image display unit 20, e.g. a computer terminal 20, as shown in FIG. 7.

A reference value dependency determining unit 19 for determining a reference value dependency RWA for the reference points R1, R2, R3 and additionally a visualization unit 19a for visualizing isolines I, a local acceptance range A and class limits KG (see subsequent figures). This visualization unit 19a is equipped as a control device for controlling a display unit 20. This controls the display unit such that isolines I, local acceptance ranges A and class limits KG are displayed.

In the example shown here, the reference value dependency determining unit 19 receives its data from the reference point determining unit 8, determines the reference value dependency RWA and passes on the data to be visualized to the output data interface 14. Embodiments are also conceivable in which the reference value dependency determining unit 19, in particular together with the visualization unit 19a, is part of the result value ascertaining unit 9.

A displacement unit 21 that is configured for a manual displacement capability for the reference points R1, R2, R3. In this example, it receives its data from the reference point determining unit 8 and supplies data regarding the displaced reference points R1, R2, R3 to the result value ascertaining unit 9, so that new result values based on the displaced reference points can be calculated. In other examples, the output of the displacement unit 21 can also be coupled to the reference value dependency determining unit 19, so that based on the displaced reference points, adapted reference value dependencies RWA can also be calculated. The displacement unit 21 can also be part of the result value ascertaining unit 9 or of the reference value dependency determining unit 19.

Figure 3:
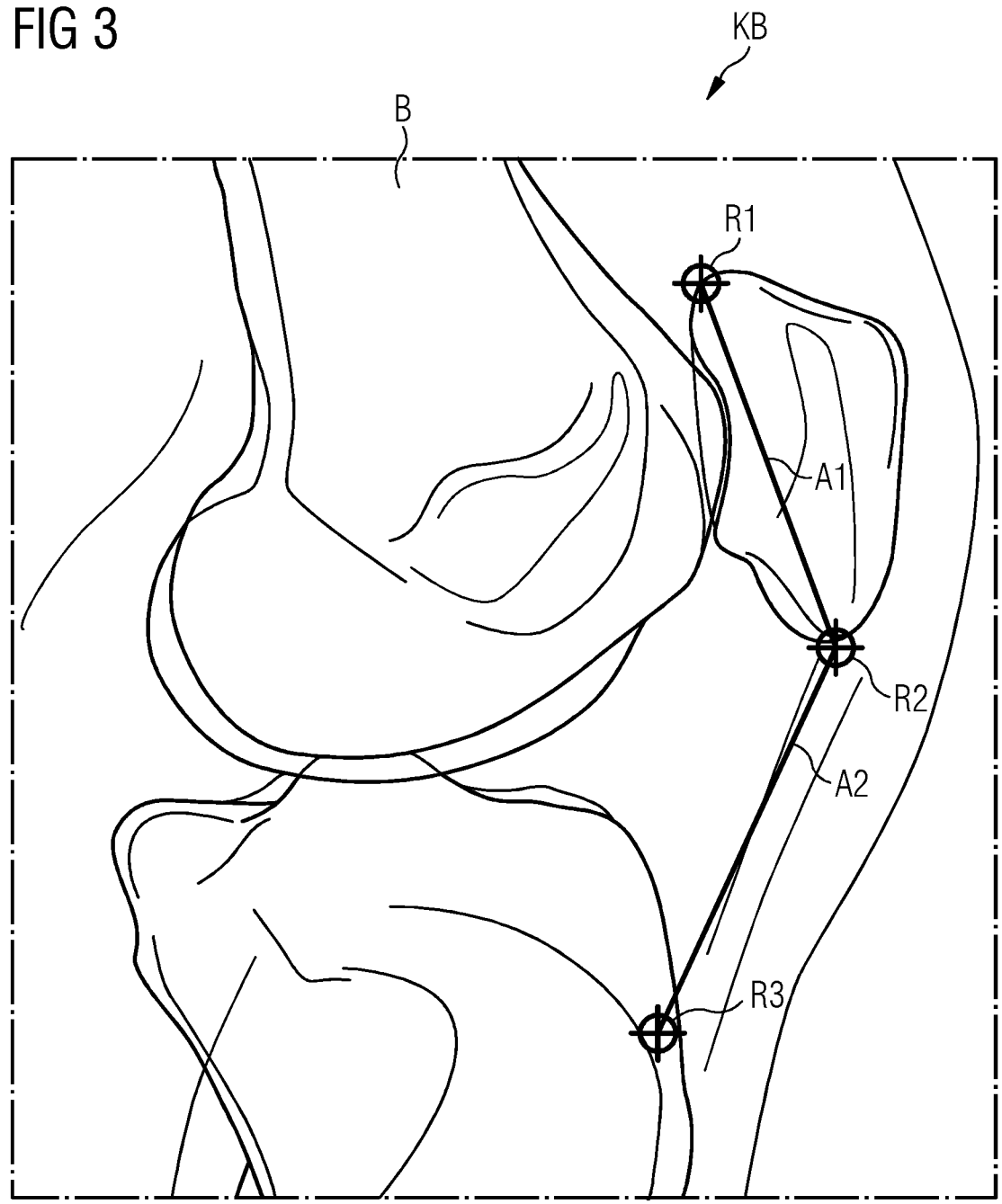
FIG. 3 is an example of a monitoring image generated by an embodiment of the invention.

FIG. 3 shows an example of a monitoring image KB generated by the invention from a skeletal image recording B of a human knee joint. In the image recording B, the points "basis patellae", "apex patellae" and "tuberositas tibiae" are marked as reference points R1, R2, R3. From the spacings A1, A2 of the reference points R1, R2, R3 shown in the drawings, as the orthopedic result value OE, for example, the Insall-Salvati index can be found from the spacing A2 shown at bottom between the apex patellae and the tuberositas tibiae divided by the upper spacing shown at top between the basis patellae and the apex patellae. The Insall-Salvati index of a healthy knee lies between 0.8 and 1.2. If an Insall-Salvati index of below 0.8 is ascertained, a patellar tendon rupture can be concluded and if it is above 1.2, a quadriceps tendon rupture could have occurred.

Figure 4:
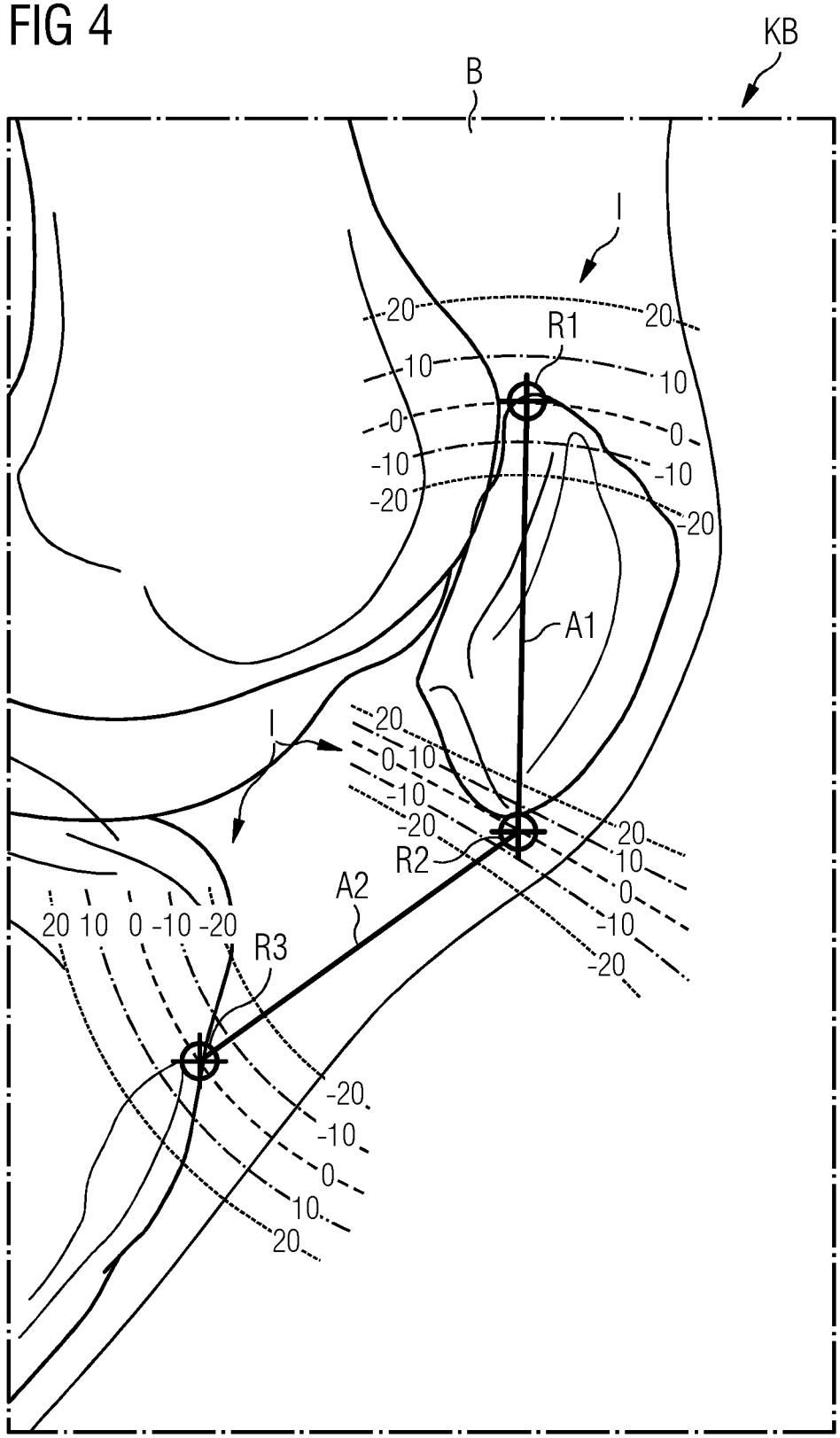
FIG. 4 is a further example of a monitoring image generated by an embodiment of the invention, comprising isolines.
Figure 5:
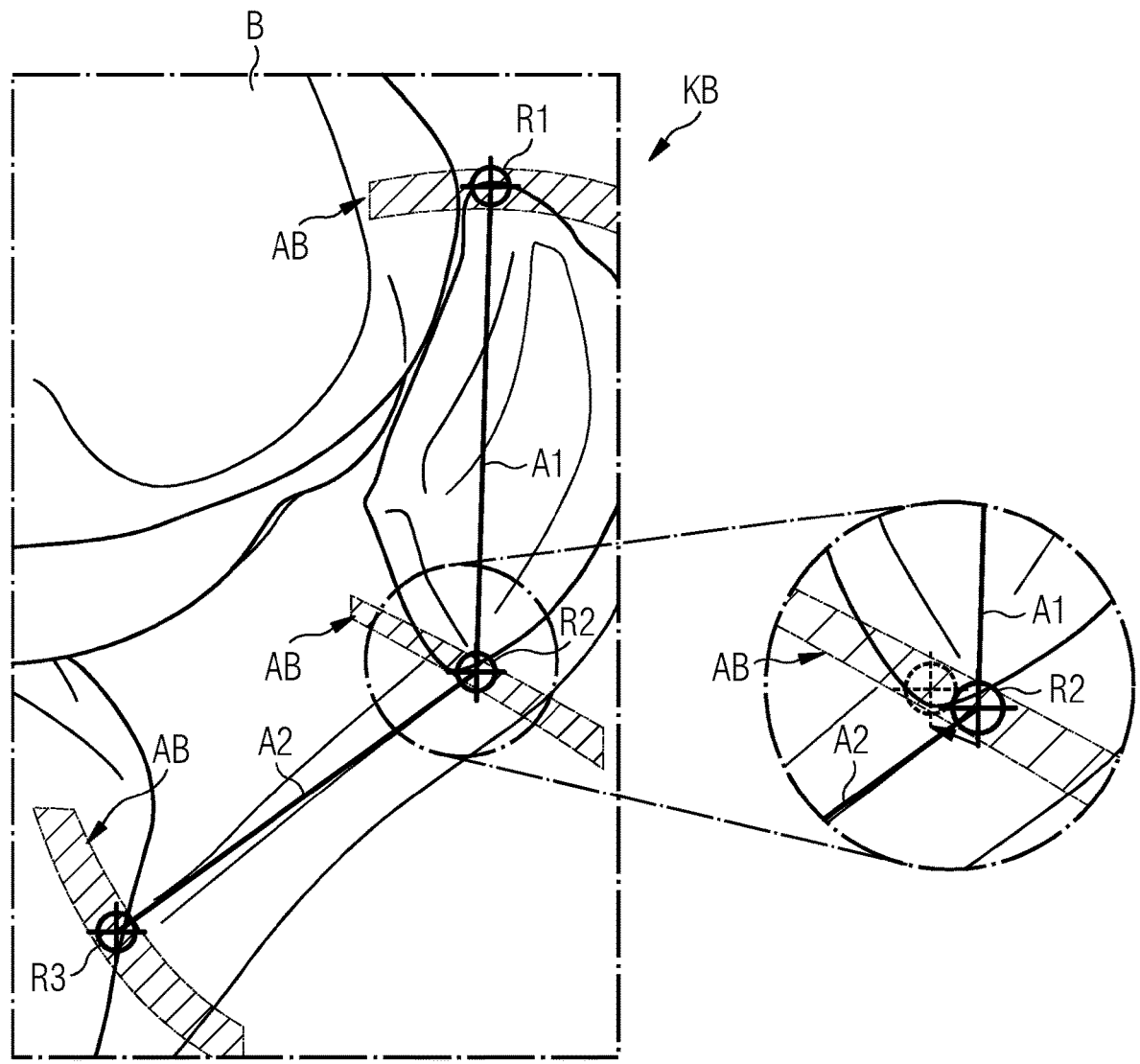
FIG. 5 is a further example of a monitoring image generated by an embodiment of the invention, comprising local acceptance ranges.
Figure 6:
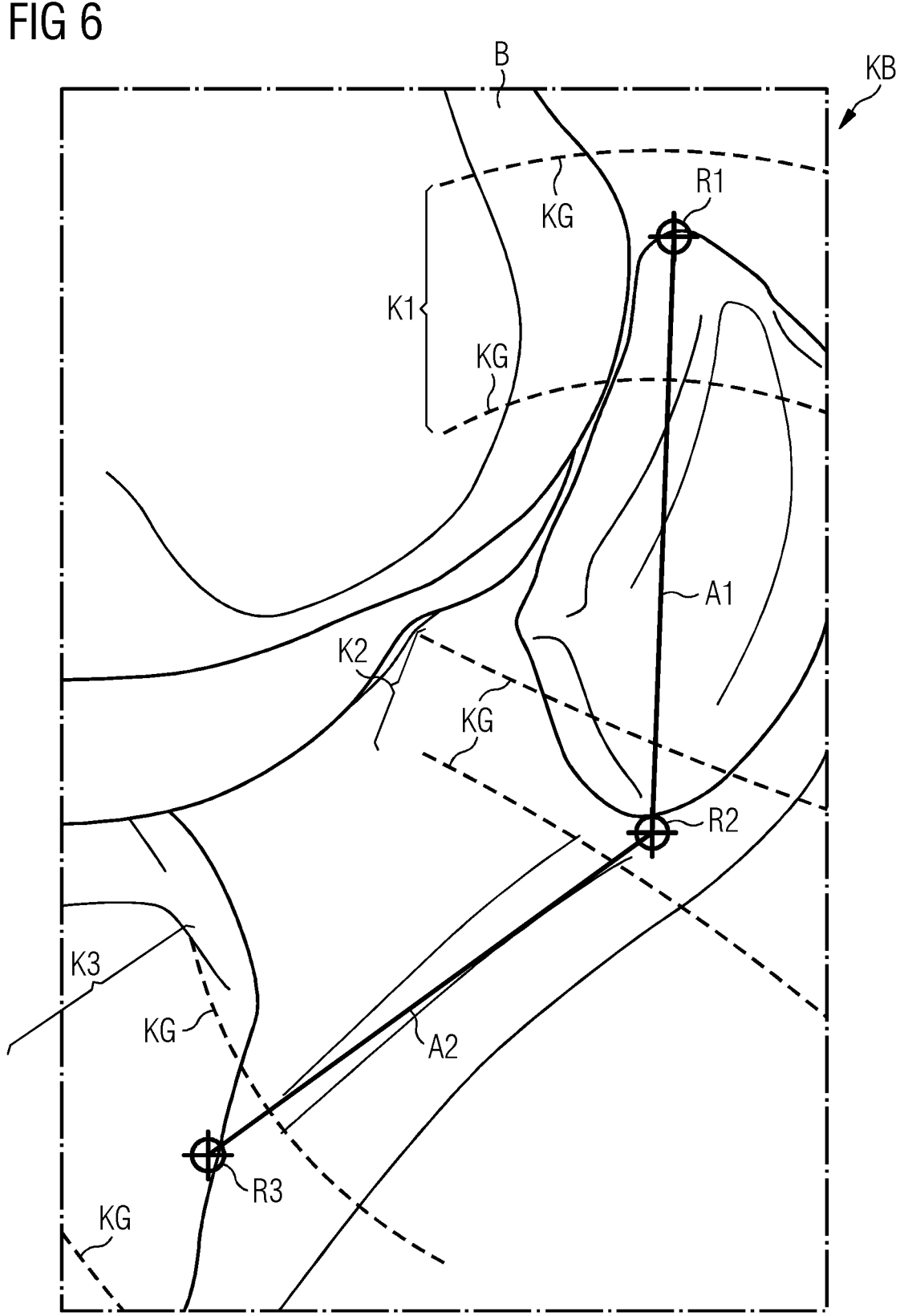
FIG. 6 is a further example of a monitoring image generated by an embodiment of the invention, comprising class limits.

In the following examples, which are illustrated by FIGS. 4, 5 and 6, exactly as in FIG. 3, an image recording B of the human knee is available in which the points basis patellae, apex patellae and tuberositas tibiae are marked as reference points R1, R2, R3 and their spacings A1, A2 are drawn in. Again, the Insall-Salvati index is considered as the orthopedic result value OE.

For each of the individual reference points R1, R2, R3, a reference value dependency RWA can now be ascertained. For the calculation of an absolute reference value dependency aRWA, for example, initially as the basic result value the Insall-Salvati index, that is, the spacing shown at bottom between the apex patellae and the tuberositas tibiae divided by the upper spacing shown at top between the basis patellae and the apex patellae for the reference points is calculated normally, and subsequently as a comparison result value, the Insall-Salvati index is calculated while one of the reference points R1, R2, R3, is respectively displaced by a displacement vector ŝ. Subsequently to these calculations, according to the above formula (1), the absolute reference value dependency aRWA for a reference point R1, R2, R3 given by $$aRWA = \text{comparison result value} - \text{basic result value}$$

is calculated.

A relative reference value dependency rRWA can be ascertained according to the above formula (2) from $$rRWA = aRWA/\text{basic result value}$$

that is, $$rRWA = (\text{comparison result value}/\text{basic result value}) - 1$$

If these calculations are now carried out for all the reference points R1, R2, R3 with a plurality of displacement vectors ŝ, then many possible reference value dependencies RWA are obtained in a region around the reference points R1, R2, R3 (which is specified by the displacement vectors ŝ).

FIG. 4 shows an example of a monitoring image KB generated by an embodiment of the invention, comprising isolines I. These isolines I provide possible displaced positions of the reference points R1, R2, R3 together with the relative reference value dependencies rRWA at these positions. In concrete terms, an isoline I extends along each of those positions at which the relative reference value dependency rRWA is the same.

The particular visualization in FIG. 4 by way of isolines I thus shows in which direction a displacement of a reference point R1, R2, R3 (a landmark) generates large changes or small changes to the result value OE. In the direction along an isoline, no change occurs, while in a direction orthogonally to the isolines, a large change takes place. In addition, in this representation, it can very easily be deduced from the monitoring image KB how strongly the change along this direction is in the event of a displacement. A large spacing between isolines I represents a relatively small change (on a displacement orthogonally to the isolines I), a smaller spacing between isolines I represents a relatively large change. Overall, a physician can thus better understand the directional dependency of displacements of the reference points R1, R2, R3 and the effects on the result value OE, and use this understanding for monitoring the landmark positions (positions of the reference points R1, R2, R3).

A great advantage is that, when monitoring the reference points R1, R2, R3, the physician can direct a high level of attention to those reference points R1, R2, R3 at which a displacement brings about a larger change of the result value OE.

FIG. 5 shows a further example of a monitoring image KB generated by an embodiment of the invention, comprising local acceptance ranges AB. This visualization reveals whether a displacement of a reference point R1, R2, R3 brings about negligible changes to the result value OE. It should be noted that simultaneous displacements of a plurality of reference points R1, R2, R3 can lead to a result value OE outside the acceptance range.

An advantage of this representation is that in a case in which a reference point R1, R2, R3 is not optimally positioned, but the alternative position lies within the local acceptance range, this is obvious to the physician with a glance at the monitoring image. As shown in the figure, the reference point R2 shown in the enlargement need not necessarily be displaced in the arrow direction to the correct position (shown dashed), since such a displacement would change nothing in the result value OE.

FIG. 6 shows a further example of a monitoring image KB generated by an embodiment of the invention, comprising class limits KG. A result value OE can be classified, in general, into the classes normal and abnormal. In the example, for each reference point R1, R2, R3, the classification range K1, K2, K3 is shown in which a position of the reference point R1, R2, R3 leads to a result value OE which still lies within the normal range. The normal ranges must be known in advance. In general, literature exists for the (where relevant, patient-dependent) definition of these normal ranges.

An advantage of this representation is that in a case in which a reference point R1, R2, R3 is not optimally positioned, but the alternative position does not bring about any change of the classification, this is obvious to the physician with a glance at the monitoring image. Thus, a displacement of the reference point R1, R2, R3 can, under some circumstances, be omitted since it is not necessary.

In the following explanation, it is assumed that the imaging system is a computed tomography system. In principle, however, the method is also usable in other imaging systems. In practice, most orthopedic measurements are done in 2D images. These can be sectional images of a CT or X-ray images which have been recorded via a radiography system.

FIG. 7 shows, in a rough schematic form, a computed tomography system 1 having a control device 10 and a diagnostic station 17, wherein both the control device 10 and the diagnostic station 17 comprise an inventive device 6 (for better clarity, shown without the components contained therein) and are thus suitable for carrying out the inventive method. The computed tomography system 1 has, in the usual way, a scanner 2 with a gantry in which there rotates an X-ray source 3 which transirradiates a patient, the patient being advanced via a support 5 into a scanning space of the gantry, so that the radiation impinges upon a detector 4 lying, in each case, opposite the X-ray source 3. It should be expressly noted that the example embodiment according to FIG. 7 is merely one example of a CT and the invention can also be used with any desired CT designs, for example with an annular, fixed X-ray detector and/or a plurality of X-ray sources.

Similarly, with the control device 10, only the components which are helpful for the explanation of the invention are shown. In principle, such CT systems and the associated control devices are known to persons skilled in the art and therefore do not need to be described in detail.

A core component of the control device 10 in this case is a processor 11 on which the different components are realized in the form of software modules. The control device 10 also has a terminal interface 14 to which a terminal 20 or a display unit 20 is connected, by which an operator can operate the control device 10 and therefore the computed tomography system 1 and, if relevant, can also view image recordings. A further interface 15 is a network interface for connecting to a data bus 21 in order thereby to create a connection to an RIS or PACS and thus to the diagnostic station 17. By way of this bus 21, for example, image recordings B can be provided for the diagnostic station 17.

By way of an interface 13, the scanner 2 can be controlled by the control device 10. By way of an acquisition interface 12, the raw data RD is read out of the detector 4. Furthermore, the control device 10 comprises a storage unit 16.

Implemented on the processor 11 as a software component is an image data reconstruction unit 18, with which from the raw data RD acquired via the data acquisition interface 12, the data desired for the image recording B is reconstructed.

The method according to an embodiment of the invention can be implemented in this example directly on the computed tomography system 1, whereby image recordings B are produced and are provided directly following their reconstruction for the method, and the monitoring images KB are displayed on the computer terminal. It is, however, also possible to process the image recordings at leisure on the diagnostic station 17 using an embodiment of the inventive method.

Finally, it should again be noted that the methods described above in detail and the devices disclosed are merely example embodiments which can be modified by a person skilled in the art in a wide variety of ways without departing from the scope of the invention. Furthermore, the use of the indefinite article "a" or "an" does not preclude the features in question also being present plurally. Similarly, the expressions "unit" and "module" do not preclude the components in question from consisting of a plurality of cooperating partial components which if necessary can also be spatially distributed.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining result values based upon a skeletal medical imaging recording, comprising:
   providing the skeletal medical imaging recording;
   automatically determining reference points in the skeletal medical imaging recording;
   calculating an orthopedic result value based upon at least one of a spacing between two reference points of the reference points determined, and an angle defined by the reference points determined; and
   determining, for a reference point of the reference points determined, a reference value dependency, representing a dependency of an orthopedic result value on a spatial displacement of the reference point.

2. The method of claim 1, further comprising:
   displaying the skeletal medical image recording together with the reference points determined within a context of a monitoring image; and
   providing a manual displacement capability for the reference points in the monitoring image.

3. The method of claim 2, wherein the displaying includes further display of at least one of the spacing between two reference points of the reference points determined, and the angle defined by the reference points determined, within the context of the monitoring image.

4. The method of claim 2, further comprising:
   displaying the reference value dependency together with the reference point.

5. The method of claim 1, wherein the determining of the reference value dependency comprises
   forming a basic result value from a group of reference points, of the reference points determined, relevant for the orthopedic result value; and
   forming a comparison result value from the group of reference points of relevance for the orthopedic result value, wherein a reference point for which the reference value dependency is determined is displaced for calculation of the comparison result value,
   wherein an absolute reference value dependency is determined from a difference of a comparison result value and a basic result value.

6. The method of claim 5, wherein a relative reference value dependency is determined from the absolute reference value dependency determined and is normalized by the basic result value, and wherein the basic result value and the comparison result value are calculated in a same way as the orthopedic result value.

7. The method of claim 1 further comprising:
   determining isolines for the reference value dependency for the reference point, the isolines identifying positions corresponding to a change of the orthopedic result value; and
   displaying the skeletal medical image recording together with the reference points determined within a context of a monitoring image, the isolines being displayed in the monitoring image.

8. The method of claim 1, further comprising:
   determining a local acceptance range for the reference value dependency for the reference point, within which a displacement of the reference point brings about a relative change of the orthopedic result value within a global acceptance range; and
   displaying the skeletal medical image recording together with the reference points determined within a context of a monitoring image, the local acceptance range being displayed in the monitoring image.

9. The method of claim 1, wherein an automatic classification at least of parts of the skeletal medical imaging recording is additionally carried out based upon at least one of the orthopedic result value and coordinates of the reference points by way of normal ranges.

10. The method of claim 9, further comprising:
    determining a reference value dependency for a reference point of the reference points determined;
    determining class limits of the reference value dependency determined, wherein within the class limits determined, displacements of the reference point bring about changes in the orthopedic result value which lie within a classification; and
    displaying the skeletal medical image recording together with the reference points determined within a context of a monitoring image, the class limits being displayed in the monitoring image.

11. The method of claim 10, further comprising:
    automatically generating a report including information items including at least one of orthopedic result values, spacings, angles, coordinates of the reference points and a classification, wherein a computer-readable file is generated, containing at least one of the information items in table form and the reference points as figures.

12. The method of claim 9, wherein the classification takes place based upon limit values defining the normal ranges, the limit values being provided in a database.

13. A non-transitory computer program product storing a computer program, directly loadable into a storage apparatus of a computer system or a diagnostic station of a medical imaging system, the computer program including program portions to carry out the method of claim 1 when the computer program is executed in the computer system or in the diagnostic station.

14. A non-transitory computer-readable medium storing program portions, readable in and executable by a computer unit, to carry out the method of claim 1 when the program portions are executed by the computer unit.

15. A device for determining result values based upon a skeletal medical imaging recording, comprising
    a data interface configured to acquire image data of the skeletal medical imaging recording;
    a reference point determining unit configured to automatically determine reference points in the skeletal medical imaging recording; and
    a result value ascertaining unit configured to calculate an orthopedic result value based upon at least one of a spacing between two reference points of the reference points determined, and an angle defined by the reference points determined
    a reference value dependency determining unit to determine, for a reference point of the reference points determined, a reference value dependency, representing a dependency of an orthopedic result value on a spatial displacement of the reference point.

16. The device of claim 15, wherein the skeletal medical image recording, together with the reference points determined, are within a context of a monitoring image, the device further comprising at least one of:
    an output data interface to output image data of the monitoring image to an image display; and
    a displacement unit configured to manually displace the reference points in the monitoring image.

17. A diagnostic station for assessing a skeletal medical imaging recording, comprising the device of claim 16.

18. A medical imaging system, comprising the device of claim 16.

19. A diagnostic station for assessing a skeletal medical imaging recording, comprising the device of claim 15.

20. A medical imaging system, comprising the diagnostic station of claim 19.

21. A medical imaging system, comprising the device of claim 15.

22. A device for determining result values based upon a skeletal medical imaging recording, comprising
- a data interface configured to acquire image data of the skeletal medical imaging recording; and
- at least one processor, configured to
  - automatically determine reference points in the skeletal medical imaging recording,
  - calculate an orthopedic result value based upon at least one of a spacing between two reference points of the reference points determined, and an angle defined by the reference points determined; and
  - determine, for a reference point of the reference points determined, a reference value dependency, representing a dependency of an orthopedic result value on a spatial displacement of the reference point.

23. A diagnostic station for assessing a skeletal medical imaging recording, comprising the device of claim 22.

24. A medical imaging system, comprising the diagnostic station of claim 23.

25. A medical imaging system, comprising the device of claim 22.

\* \* \* \* \*